US010948478B2

(12) United States Patent
Brun et al.

(10) Patent No.: US 10,948,478 B2
(45) Date of Patent: *Mar. 16, 2021

(54) BLOOD STATE ANALYSIS DEVICE, BLOOD STATE ANALYSIS SYSTEM, BLOOD STATE ANALYSIS METHOD, AND PROGRAM

(71) Applicant: Sony Corporation, Tokyo (JP)

(72) Inventors: Marcaurele Brun, Tokyo (JP); Yoshihito Hayashi, Chiba (JP)

(73) Assignee: Sony Corporation, Tokyo (JP)

( * ) Notice: Subject to any disclaimer, the term of this patent is extended or adjusted under 35 U.S.C. 154(b) by 746 days.

This patent is subject to a terminal disclaimer.

(21) Appl. No.: 14/777,906

(22) PCT Filed: Feb. 18, 2014

(86) PCT No.: PCT/JP2014/053707
§ 371 (c)(1),
(2) Date: Sep. 17, 2015

(87) PCT Pub. No.: WO2014/156371
PCT Pub. Date: Oct. 2, 2014

(65) Prior Publication Data
US 2016/0299124 A1    Oct. 13, 2016

(30) Foreign Application Priority Data

Mar. 29, 2013 (JP) .............................. JP2013-073831
Dec. 20, 2013 (JP) .............................. JP2013-263565

(51) Int. Cl.
*G01N 33/49* (2006.01)
*G01N 27/02* (2006.01)
*G01N 33/487* (2006.01)

(52) U.S. Cl.
CPC ....... *G01N 33/4905* (2013.01); *G01N 27/026* (2013.01); *G01N 33/48707* (2013.01)

(58) Field of Classification Search
None
See application file for complete search history.

(56) References Cited

U.S. PATENT DOCUMENTS

| 8,132,446 | B2 | 3/2012 | Hayashi |
| 8,478,546 | B2 | 7/2013 | Katsumoto et al. |
| 9,097,635 | B2 | 8/2015 | Hayashi |
| 9,915,599 | B2 | 3/2018 | Brun et al. |
| 9,952,168 | B2 | 4/2018 | Brun et al. |
| 10,393,761 | B2 * | 8/2019 | Hayashi ................ G01N 33/86 |
| 10,527,605 | B2 | 1/2020 | Brun et al. |
| 10,648,936 | B2 | 5/2020 | Hayashi et al. |
| 10,801,980 | B2 | 10/2020 | Brun et al. |
| 2009/0293595 | A1 | 12/2009 | Hayashi |
| 2010/0136606 | A1 | 6/2010 | Katsumoto et al. |
| 2012/0035450 | A1 | 2/2012 | Hayashi |
| 2012/0137753 | A1 | 6/2012 | Hayashi |
| 2012/0238026 | A1 | 9/2012 | Hayashi et al. |
| 2015/0323480 | A1 | 11/2015 | Brun et al. |
| 2015/0346125 | A1 | 12/2015 | Hayashi et al. |
| 2015/0377763 | A1 | 12/2015 | Brun et al. |
| 2016/0011170 | A1 | 1/2016 | Brun et al. |
| 2016/0018346 | A1 | 1/2016 | Hayashi et al. |
| 2016/0025610 | A1 | 1/2016 | Katsumoto et al. |
| 2016/0282366 | A1 | 9/2016 | Hayashi et al. |
| 2016/0299124 | A1 | 10/2016 | Brun et al. |
| 2018/0202955 | A1 | 7/2018 | Brun et al. |
| 2020/0096497 | A1 | 3/2020 | Brun et al. |
| 2020/0174027 | A1 | 6/2020 | Hayashi et al. |

FOREIGN PATENT DOCUMENTS

| EP | 2 375 244 A1 | 10/2011 |
| EP | 2 500 726 A1 | 9/2012 |
| JP | 62-153761 A2 | 7/1987 |
| JP | 63-133062 A2 | 6/1988 |
| JP | 2010-181400 A | 8/2010 |
| JP | 2012-194087 A | 10/2012 |
| WO | WO 2010/079845 A1 | 7/2010 |

OTHER PUBLICATIONS

Uchimora et al., "Dielectric spectroscopy measurement of blood coagulation in diabetes mellitus" (Diabetes Abstract No. 2216-PO (2010)).*
Hayashi et al., An Approach for Risk Assessment of Venous Thrombosis Using Dielectric Spectroscopy [Jomyaku Kessensho no Risk Hyoka ni Muketa Yuden Bunkoho ni yoru Approach], Dai 32 Kai Japanese Society of Biorheology Nenkai Program Shorokushu, May 18, 2009;p75.
Irimajiri et al., Dielectric monitoring of rouleaux formation in human whole blood: a feasibility study, Biochimica et Biophysica Acta, 1996; 1290:207-9.
Irimajiri et al., Hemagglutination (rouleau formation) judging from dielectric behavior of the whole blood [Zenketsu no Yuden Kyodo kara Mita Sekkekkyu Gyoshu (Rensen Keisei)], Biotechnology, 2000;78(5):162-5.
Uchimura et al., Measurement of Blood Coagulation by Dielectric Spectroscopy and its Application to Diabetes [Yuden Bunkoho ni yoru Ketsueki Gyoko Sokutei to Tonyobyo eno Oyo], the 1st International Symposium of Biorheology, The 33rd Annual Meeting of the Japanese Society of Biorheology Program-shu. May 28, 2010; p99.

(Continued)

*Primary Examiner* — Nancy J Leith
(74) *Attorney, Agent, or Firm* — Wolf, Greenfield & Sacks, P.C.

(57) ABSTRACT

A blood state analysis device, blood state analysis system, blood state analysis method, and program that enable analysis of the state of blood easily and precisely is provided. The blood state analysis device includes: an extraction unit configured to extract at least one feature from chronological change data of an electrical characteristic of blood in two or more frequency bands; an evaluation unit configured to evaluate a state of the blood on the basis of the at least one feature extracted by the extraction unit; and a classification unit configured to classify the blood on the basis of a result of evaluation conducted by the evaluation unit.

14 Claims, 16 Drawing Sheets

(56) References Cited

OTHER PUBLICATIONS

International Search Report and Written Opinion and English translation thereof dated May 20, 2014 in connection with International Application No. PCT/JP2014/053707.
International Preliminary Report on Patentability and English translation thereof dated Oct. 8, 2015 in connection with International Application No. PCT/JP2014/053707.
Japanese Office Action dated Jul. 29, 2020 in connection with Japanese Application No. 2019-074663, and English translation thereof.

* cited by examiner

FIG.2
A
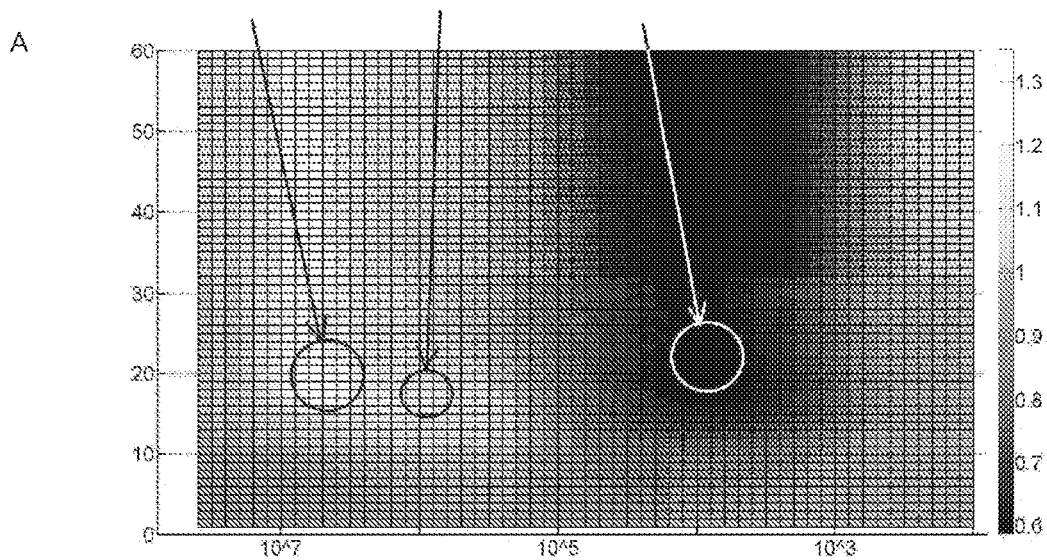
B
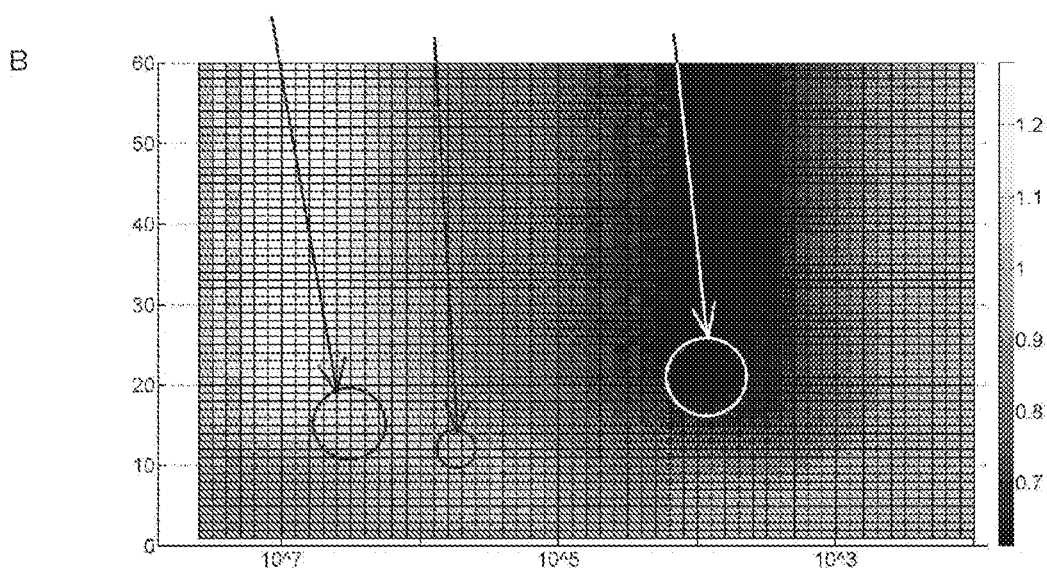

BLOOD STATE ANALYSIS DEVICE, BLOOD STATE ANALYSIS SYSTEM, BLOOD STATE ANALYSIS METHOD, AND PROGRAM

CROSS-REFERENCE TO RELATED APPLICATIONS

This application is a National Stage of International Application No. PCT/JP2014/053707, filed in the Japanese Patent Office as a Receiving office on Feb. 18, 2014, which claims priority to Japanese Patent Application Number 2013-263565, filed in the Japanese Patent Office on Dec. 20, 2013 and Japanese Patent Application Number 2013-073831, filed in the Japanese Patent Office on Mar. 29, 2013, each of which is hereby incorporated by reference in its entirety.

TECHNICAL FIELD

The present technology relates to a blood state analysis device, a blood state analysis system, a blood state analysis method, and a program. More specifically, the present technology relates to a technology for analyzing a state of blood from an electrical characteristic thereof.

BACKGROUND ART

Anti-platelet aggregation agents or anti-coagulant agents are prophylactically administered to patients or healthy persons who have thrombosis risks. Examples of the patients having thrombus formation risks include patients with diabetes, arteriosclerosis, cancer, heart disease, and respiratory disease; perioperative patients; and patients taking immunosuppressants. Also, examples of the healthy persons having thrombus risks include pregnant women and elderly people. As the anti-platelet aggregation agents, acetylsalicylic acid and the like are used; and as the anti-coagulant agents, warfarin, heparin, activated blood coagulation factor Xa inhibitors, direct thrombin inhibitors, and the like are used.

The prophylactic administration of anti-platelet aggregation agents and anti-coagulant agents against thrombosis has the side effect that an excessively high administered dose increases a bleeding risk. In order to obtain a sufficient prophylactic effect while inhibiting this side effect, an administration management becomes important in which blood coagulability of an administered subject is timely evaluated, and the drug and dose to be administered are appropriately selected and determined.

A method for a blood coagulability test for managing drug administration includes the prothrombin time-international normalized ratio (PT-INR), the activated partial thromboplastin time (APTT), and the like. Also, a method for a platelet aggregation test includes adding a substance that induces aggregation of platelet to platelet rich plasma (PRP) obtained by centrifuging blood, and measuring a change in transmitted light levels or absorbance associated with the aggregation to determine good or poor in aggregation capacity.

In recent years, techniques for obtaining information related to a blood coagulation system from dielectric permittivity of blood have been proposed (see Patent Literatures 1 and 2). For example, in blood coagulation system analysis devices disclosed in Patent Literatures 1 and 2, blood to be analyzed is held in a container provided with electrodes so that a voltage can be applied to the blood, and an alternating current is applied to the electrodes to measure complex dielectric permittivity. In these devices, by analyzing a complex dielectric permittivity spectrum obtained by the measurement according to a predetermined algorithm, enhancement or reduction of blood coagulability such as a blood coagulation time is evaluated.

CITATION LIST

Patent Literature

Patent Literature 1: JP 2010-181400A
Patent Literature 2: JP 2012-194087A

SUMMARY OF INVENTION

Technical Problem

However, known blood coagulability tests such as PT-INR and APTT substantially evaluate only the bleeding risk associated with reduction in blood coagulability caused by excess administration of anti-coagulant agents, and cannot evaluate the thrombus risk associated with enhancement in blood coagulability. Also, the existing platelet aggregation test using PRP may require a centrifugation process. This may cause platelet to be activated during this process, thereby inhibiting accurate test results from being obtained. Furthermore, the operation is complicated.

In contrast, the techniques for measuring dielectric permittivity of blood disclosed in Patent Literatures 1 and 2 can obtain information related to blood coagulability or the like easily and accurately. However, other states of blood are not considered. Thus, a technique for analyzing the state of blood such as a thrombosis risk easily and precisely has been demanded.

Accordingly, the present disclosure mainly aims to provide a blood state analysis device, blood state analysis system, blood state analysis method, and program that enable analysis of the state of blood easily and precisely.

Solution to Problem

The present inventors have intensely considered and tested a solution to the above-described problem, and then found that the state of blood such as the thrombosis risk is analyzed easily and precisely by using data of an electrical characteristic of blood measured by an electrical characteristic measurement device such as the above-described dielectric coagulometer, and arrived at the present invention.

That is, a blood state analysis device according to the present disclosure includes at least: an extraction unit configured to extract at least one feature from chronological change data of an electrical characteristic of blood in two or more frequency bands; an evaluation unit configured to evaluate a state of the blood on the basis of the at least one feature extracted by the extraction unit; and a classification unit configured to classify the blood on the basis of a result of evaluation conducted by the evaluation unit.

The evaluation unit may digitalize the at least one extracted feature for each frequency band.

In addition, the classification unit may classify the blood by use of a numerical value representing the at least one feature.

The classification unit may also classify the blood by comparing the numerical value with a predetermined threshold.

For example, the numerical value is a change amount $\delta A$ ($=A(f_x,t_y)/A(f_x,t_a)$) of an electrical characteristic value A in a given frequency $f_x$ from a reference time $t_a$ to a given time $t_y$.

The at least one feature is, for example, a distinctive time associated with a change in a state of the blood.

The classification unit may classify the blood by use of a number of change points in a frequency gradient and/or a direction in which the frequency gradient changes.

The classification unit may also classify the blood by comparing features of each frequency band graphically.

The blood state analysis device may further include a measurement unit configured to chronologically measure the electrical characteristic of the blood, which is an analysis target, in a particular frequency or frequency band.

In this case, a data processing unit configured to remove noise from the chronological change data of the electrical characteristic of the blood, which has been measured by the measurement unit, may be provided.

A blood state analysis system according to the present disclosure includes: an electrical characteristic measurement device including a measurement unit configured to chronologically measure an electrical characteristic of blood, which is an analysis target, in a particular frequency or frequency band; and a blood state analysis device including at least an extraction unit configured to extract a feature from chronological change data of the electrical characteristic of the blood, which has been measured by the electrical characteristic measurement device, in two or more frequency bands, an evaluation unit configured to evaluate the blood on the basis of the feature extracted by the extraction unit, and a classification unit configured to classify the blood on the basis of a result of evaluation conducted by the evaluation unit.

The blood state analysis system may further include a server including an information storage unit configured to store information of at least one of a result of measurement in the electrical characteristic measurement device, the feature extracted by the extraction unit of the blood state analysis device, the result of evaluation in the evaluation unit of the blood state analysis device, and a result of classification in the classification unit of the blood state analysis device, in which the server is connected to the electrical characteristic measurement device and/or the blood state analysis device through a network.

A blood state analysis method according to the present disclosure includes: an extraction step of extracting a feature from chronological change data of an electrical characteristic of blood in two or more frequency bands; an evaluation step of evaluating the blood on the basis of the feature extracted by the extraction unit; and a classification step of classifying the blood on the basis of a result of evaluation conducted by the evaluation unit.

A program according to the present disclosure is a program for causing a computer to execute: an extraction function of extracting a feature from chronological change data of an electrical characteristic of blood in two or more frequency bands; an evaluation function of evaluating the blood on the basis of the extracted feature; and a classification function of classifying the blood on the basis of a result of evaluation.

Advantageous Effects of Invention

According to the present disclosure, since the blood is evaluated and classified by use of a feature extracted from chronological change data of an electrical characteristic, it becomes possible to analyze the state of blood precisely by a simple method. Note that the effects described here are not necessarily limiting, and any of these effects described in the present disclosure may be exhibited.

BRIEF DESCRIPTION OF DRAWINGS

FIG. 2A and B are diagrams illustrating change points in frequency gradients in a typical coagulation state with horizontal axes representing frequencies and vertical axes representing times.

DESCRIPTION OF EMBODIMENTS

Embodiments for implementing the present disclosure will be described in detail below with reference to the appended drawings. Note that the present disclosure is not limited to each embodiment described below. The description will be made in the following order.

1. First Embodiment (Example of Blood State Analysis Device that Classifies Blood from Chronological Change in Electrical Characteristic)

2. Modification Example of First Embodiment (Example of Blood State Analysis Device Including Measurement Unit and Data Processing Unit)

3. Third Embodiment (Example of Blood State Analysis System)

1. First Embodiment

Figure 1:
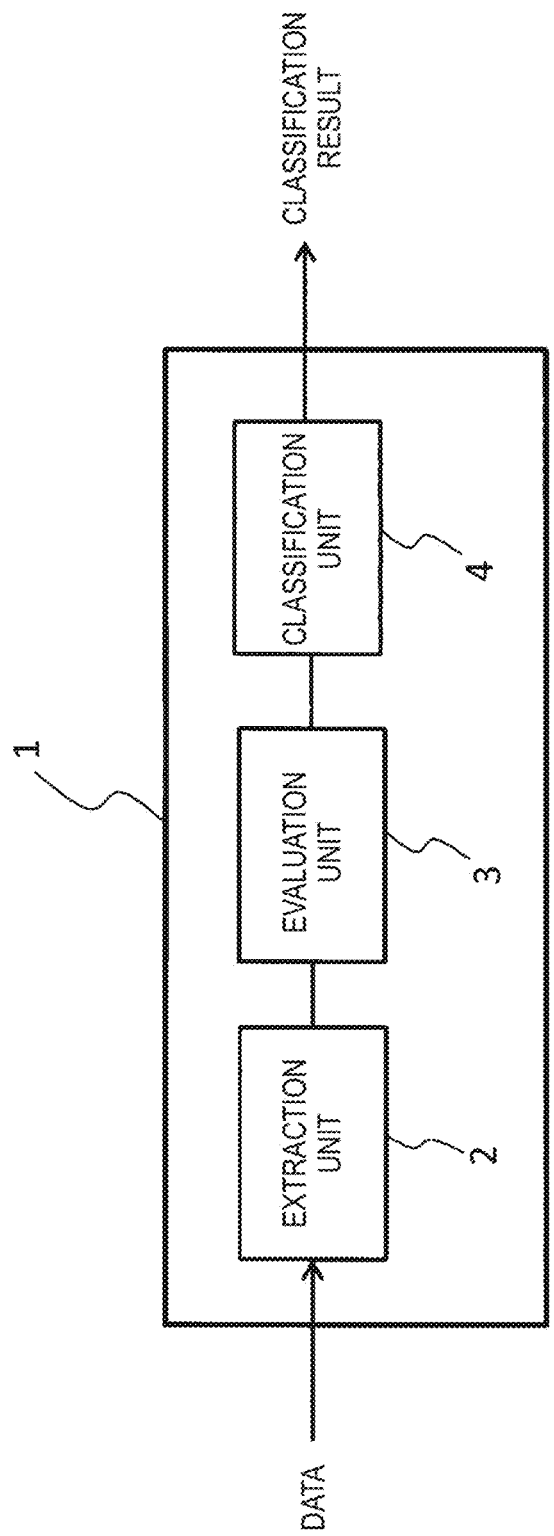
FIG. 1 is a block diagram illustrating a configuration example of a blood state analysis device according to a first embodiment of the present disclosure.

First, a blood state analysis device according to a first embodiment of the present disclosure will be described. FIG. 1 is a block diagram illustrating a configuration example of the blood state analysis device according to the present embodiment. As illustrated in FIG. 1, a blood state analysis device 1 according to the present embodiment includes at least an extraction unit 2, an evaluation unit 3, and a classification unit 4.

Extraction Unit 2

The extraction unit 2 extracts a feature from chronological change data of an electrical characteristic of blood being an analysis target, in two or more frequency bands. The "electrical characteristic" mentioned here include, for example, impedance, conductance, admittance, capacitance, dielectric permittivity, conductivity, phase angle, and a quantity obtained by converting such a value into a quantity of electricity. In addition, the "feature" here includes not only a distinctive value calculated from chronological change data of an electrical characteristic, but also a graphical feature extracted from a display image of chronological change data.

Note that the blood state analysis device 1 according to the present embodiment can evaluate and classify blood by use of one of the above-described electrical characteristic, and can also use two or more electrical characteristics. In addition, the feature extracted in the extraction unit 2 is not limited to one feature, but two or more features may be extracted.

The feature extracted by the extraction unit 2 include a distinctive time associated with a change in the state of blood, a change amount of an electrical characteristic value, a change point of a frequency gradient, and the like. In addition, specific examples of distinctive times associated with a change in the state of blood include blood coagulation start time, blood coagulation end time, erythrocyte sedimentation start time, erythrocyte sedimentation end time, erythrocyte rouleaux formation start time, and erythrocyte rouleaux formation end time.

Evaluation Unit 3

The evaluation unit 3 evaluates the state of blood on the basis of the feature extracted by the extraction unit 2. Examples of the states of blood as an evaluation target include blood coagulation state, aggregation state of ingredients of blood, erythrocyte sedimentation or rouleaux state, and blood clot shrinkage state.

A method for evaluating the state of blood is not particularly limited, and may be selected as appropriate in accordance with the feature extracted by the extraction unit 2. For example, in a case of evaluating the blood coagulation state, a method of digitalizing the extracted feature for each frequency band may be employed. In a case where the extracted feature is graphical, for example, the evaluation unit 3 compares reference data and extracted data graphically with each other.

Classification Unit 4

Figure 3:
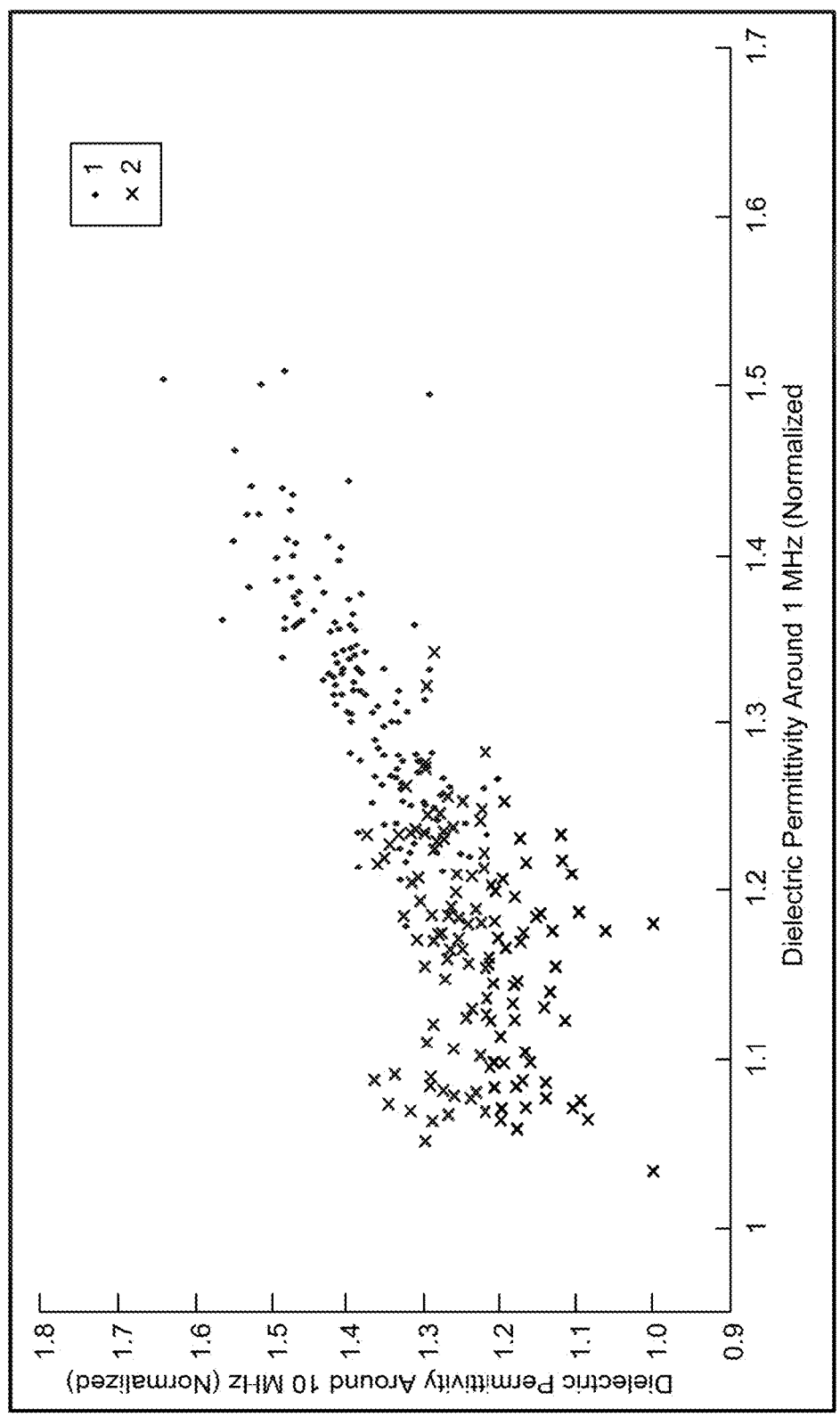
FIG. 3 is a diagram illustrating an example of a classification method by use of a value in a particular frequency.

The classification unit 4 classifies blood on the basis of the result of evaluation conducted by the evaluation unit 3. FIG. 2 and FIG. 3 illustrate classification examples. In this event, there is no particular limitation on the method for classifying blood. For example, a method or classifying blood by comparing the numerical value obtained by the evaluation unit 3 with a predetermined threshold may be employed.

The classification may be alternatively performed by use of the number of change points in a frequency gradient, the direction in which the frequency gradient changes, or both, illustrated in FIG. 2A and FIG. 2B. In addition, the classification may be performed by use of a value in a particular frequency as illustrated in FIG. 3. Furthermore, the classification unit 4 may classify the blood by comparing features graphically in each frequency band, such as spectral patterns.

Operation

Figure 4:
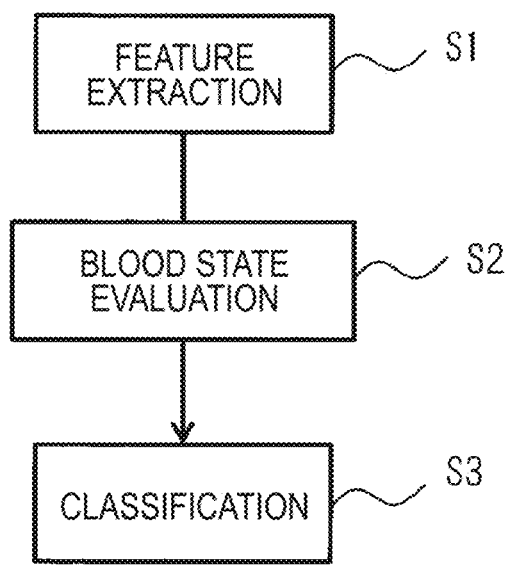
FIG. 4 is a flowchart illustrating a method for analyzing a state of blood by use of a blood state analysis device illustrated in FIG. 1, in the order of steps.
Figure 5:
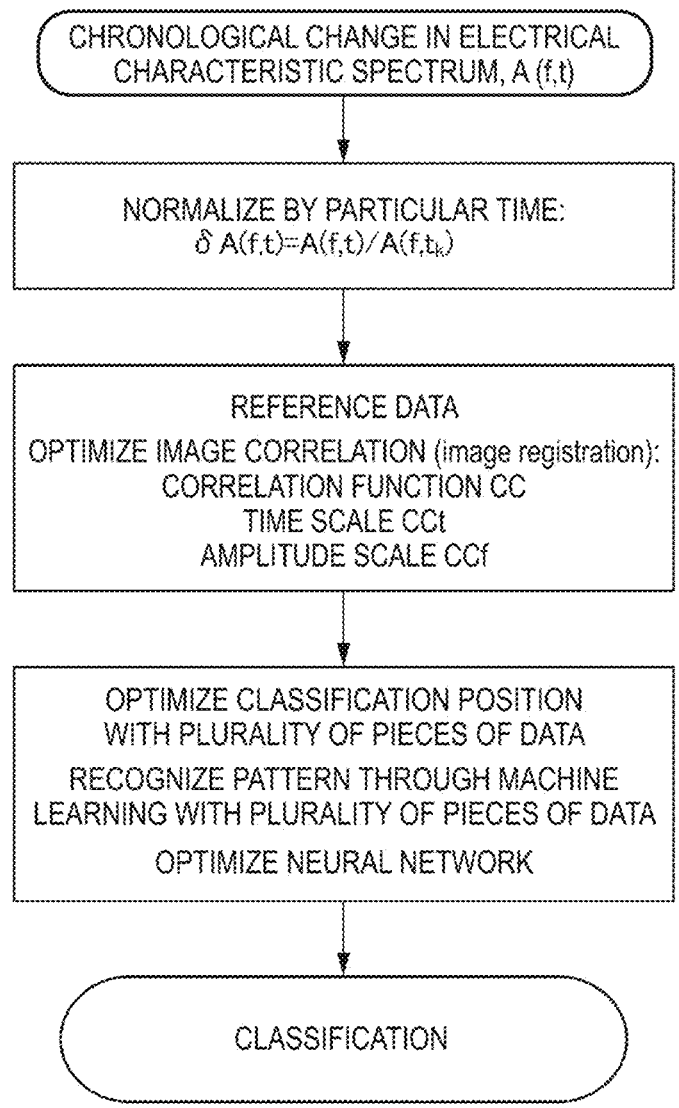
FIG. 5 is a flowchart illustrating an operation example.

Next, an operation of the above-described blood state analysis device 1, that is, a method for evaluating and classifying the state of blood by use of the blood state analysis device 1, will be described. FIG. 4 is a flowchart illustrating a method for analyzing the state of blood by use of the blood state analysis device 1 illustrated in FIG. 1, in the order of steps, and FIG. 5 is a flowchart illustrating an operation example.

Step S1: Feature Extraction Step

In the blood state analysis device 1 according to the present embodiment, first, in the extraction unit 2, a feature is extracted in two or more frequency bands from chronological change data A (f,t) in an electrical characteristic of blood (step S1). In this event, the frequency bands in which the feature is extracted can be selected as appropriate in accordance with the state of blood to be evaluated. However, it is preferable to select the frequency bands from a range of 100 Hz to 100 MHz, more preferably from a range of 1 kHz to 10 MHz, in which the influence of protein is relatively low.

For example, in a case where the electrical characteristic is dielectric permittivity and a venous thromboembolism (VTE) risk of blood being an analysis target is predicted, the feature is extracted in around 10 MHz, around 1 MHz, and around 2.5 kHz. In blood positive for venous thromboembolism (VTE), in a high frequency band (higher than or equal to 3 MHz and lower than or equal to 30 MHz) around 10 MHz, an increase can be seen in dielectric permittivity (a real part of complex dielectric permittivity) associated with blood coagulation. In addition, in a middle frequency band (higher than or equal to 100 kHz and lower than 3 MHz) around 1 MHz, an increase can be seen in dielectric permittivity (a real part of complex dielectric permittivity) due to erythrocyte rouleaux formation. Furthermore, in blood of elevated blood sedimentation, a peak indicating sedimentation can be seen around 2.5 kHz.

On the other hand, the blood negative for thrombosis has the following two feature patterns. A first pattern is a case where the increase in dielectric permittivity (a real part of complex dielectric permittivity) can be seen in a low frequency band, unlikely in positive blood. A second pattern is a case where the increase in dielectric permittivity (a real part of complex dielectric permittivity) associated with blood coagulation and the following decrease are observed separately from the increase in dielectric permittivity (a real part of complex dielectric permittivity) due to the above-described erythrocyte rouleaux formation in a middle frequency band. The second pattern that is feature in the middle frequency band may be a distinctive change as in blood of a healthy person. States of blood and frequency bands in which distinctive changes can be seen in dielectric permittivity (a real part of complex dielectric permittivity) are illustrated in Table 1 below.

TABLE 1

| State of Blood | Frequency Band in which Change in Dielectric Permittivity Is Seen | Frequency Band in which Change in Dielectric Permittivity Is More Significant |
|---|---|---|
| Coagulation (Blood Coagulation) | 1 kHz to 50 MHz | 3 MHz to 15 MHz |
| Aggregation | 1 kHz to 50 MHz | 500 kHz to 5 MHz |
| Fibrin Formation | 1 kHz to 50 MHz | 3 MHz to 15 MHz |
| Fibrin Clot Formation | 1 kHz to 50 MHz | 3 MHz to 15 MHz |
| Blood Clot Formation | 1 kHz to 50 MHz | 3 MHz to 15 MHz |
| Erythrocyte Rouleaux Formation | 500 kHz to 25 MHz | 2 MHz to 10 MHz |
| Erythrocyte Sedimentation | 1 kHz to 50 MHz | 100 kHz to 40 MHz |
| Blood Clot Retraction | 1 kHz to 50 MHz | 10 kHz to 100 kHz |
| Hemolysis | 1 kHz to 50 MHz | 3 MHz to 15 MHz |
| Fibrinolysis | 1 kHz to 50 MHz | 3 MHz to 15 MHz |

As illustrated in Table 1, when a feature is extracted in a range of 3 kHz to 15 MHz from chronological change data of dielectric permittivity of blood, for example, states of blood coagulation, fibrin formation, fibrin clot formation, blood clot formation, hemolysis, and fibrinolysis can be evaluated highly precisely. In addition, the feature of the aggregation of blood is extracted in a range of 500 kHz to 5 MHz, that of erythrocyte rouleaux formation is extracted in a range of 2 MHz to 10 MHz, that of blood sedimentation is extracted in a range of 100 kHz to 40 MHz, and that of blood clot retraction is extracted in a range of 10 kHz to 100 kHz, from chronological change data of dielectric permittivity.

Step S2: Blood State Evaluation Step

Next, on the basis of the feature extracted by the extraction unit 2, the state of blood is evaluated in the evaluation unit 3 (step S2). The state of blood may be evaluated by digitalizing chronological change data of the electrical characteristic, for example.

There is no particular limitation on a method for digitalizing chronological change data of the electrical characteristic. For example, there is a method for normalizing chronological change data of the electrical characteristic by a particular time to obtain a change amount δA (f,t) expressed by the following formula 1. Note that A (f,$t_a$) in the following formula 1 is a change amount of the electrical characteristic in a given frequency f at a reference time $t_a$.

$$\delta A(f, t) = A(f, t)/A(f, t_a) \quad \text{[Math 1]}$$

Then, the change amount δA (f,t) calculated from the above formula 1 is differentiated with respect to frequency or time, for example, and local extreme values, a differential amplitude, an angle, and the like are obtained, thereby conducting evaluation.

Alternatively, the evaluation may be conducted by using a determination value p1 calculated from the following formula 2. This determination value $p_1$ is calculated from a change amount δA ($f_1$,$t_1$) in the electrical characteristic in a first frequency $f_1$ at a first time $t_1$, a change amount δA ($f_2$,$t_1$) in the electrical characteristic in a second frequency $f_2$ at the first time $t_1$, and a change δA ($f_3$,$t_i$) in the electrical characteristic in a third frequency $f_3$ at the first time $t_1$.

$$p_1 = \{\delta A(f_1, t_1)\}^2 \times \{\delta A(f_2, t_1)\}^2 / \{\delta A(f_3, t_1)\}^2 \times t_1$$
wherein f1<$f_2$<$f_3$. [Math 2]

Alternatively, the evaluation may be conducted by using a determination value p2 calculated from the following formula 3.

$$p_2 = \{\delta A(f_1, t_1) \times \delta A(f_3, t_1)\}/\{\delta A(f_2, t_1) \times t_1\} \text{ wherein}$$
$f_1$<$f_2$<$f_3$. [Math 3]

Further alternatively, without normalizing the chronological change data of the electrical characteristic by a particular time, fitting may be performed by using the following formula 4 and formula 5.

$$A(f, t_i) = \frac{a_0(t_i) + a_1(t_i)f + a_2(t_i)f^2 + a_3(t_i)f^3 + a_4(t_i)f^4 + a_5(t_i)f^5 + \ldots + a_n(t_i)f^n}{a_{n+1}(t_i) + a_{n+2}(t_i)f + \ldots + a_{n+m+1}(t_i)f^m} \quad \text{[Math 4]}$$

$$a_i(t) = \frac{a_{i,0} + a_{i,1}t + a_{i,2}t^2 + a_{i,3}t^3 + \ldots + a_{i,p}t^p}{a_{i,p+1} + a_{i,p+2}t + \ldots + a_{i,q}t^q} \quad \text{[Math 5]}$$

Step S3: Classification Step

Next, on the basis of the result of evaluation in the evaluation unit 3, blood is classified in the classification unit 4. In this event, a classification method may be selected as appropriate in accordance with the evaluation method in the evaluation unit 3. For example, in a case where the determination values $p_1$ and $p_2$ are calculated in the evaluation unit 3, by comparing the determination values $p_1$ and $p_2$ with a predetermined threshold, it is possible to classify blood easily in accordance with the state thereof.

In a case where the evaluation result is image data such as a spectral shape, by comparing feature parameters of blood being the analysis target with feature parameters of reference data by an image recognition technique, classification is possible.

The above-described steps of S1 to S3 can be conducted by creating and mounting, in a personal computer for example, a computer program for achieving the functions of an information processing apparatus. Such a computer program may also be stored in a recording medium such as a magnetic disk, an optical disc, a magneto-optical disk, or a flash memory, or may be distributed through a network.

As specifically described above, in the blood state analysis device according to the present embodiment, by use of the feature extracted from chronological change data of the electrical characteristic, blood is evaluated and classified. Therefore, the state of blood can be analyzed highly precisely by a simple method. This technique can also be useful in pathological examination in addition to the research field.

2. Modification Example of First Embodiment

Figure 6:
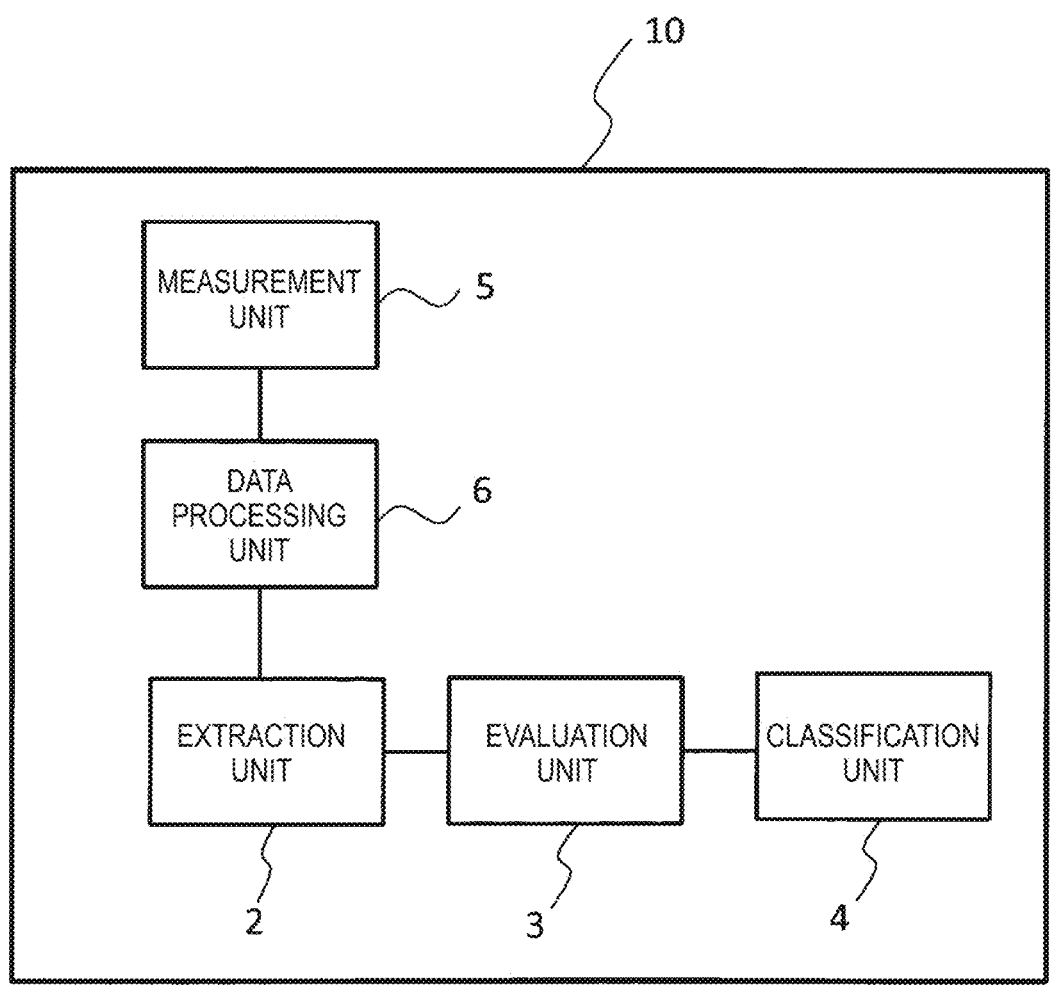
FIG. 6 is a block diagram illustrating a configuration example of a blood state analysis device according to a modification example of the first embodiment of the present disclosure.

Next, a blood state analysis device according to a modification example of the first embodiment of the present disclosure will be described. FIG. 6 is a block diagram illustrating a configuration example of the blood state analysis device according to the present embodiment. Note that in FIG. 6, the same structural elements as those in the blood state analysis device 1 illustrated in FIG. 1 are denoted by the same reference numerals, and a detailed description thereof will be omitted.

As illustrated in FIG. 6, a blood state analysis device 10 according to the modification example includes, in addition to the above-described extraction unit 2, evaluation unit 3, and classification unit 4, a measurement unit 5 and a data processing unit 6. The blood state analysis device 10 can also be provided with a display unit (not illustrated) and a storage unit (not illustrated).

Measurement Unit 5

The measurement unit 5 chronologically measures an electrical characteristic of blood, which is an analysis target, in a particular frequency or frequency band. The electrical characteristic measured by the measurement unit 5 include, for example, impedance, conductance, admittance, capacitance, dielectric permittivity, conductivity, phase angle, and a quantity obtained by converting such a value into a quantity of electricity. The blood state analysis device 10 according to the modification example can conduct evaluation and classification by using one of these electrical characteristics, but may also use two or more electrical characteristics.

A configuration of the measurement unit 5 is not particularly limited, and may be appropriately determined depending on the electrical characteristic to be measured. For example, when an alternating voltage is applied between a pair of electrodes provided in a sample container to measure the impedance and dielectric permittivity of blood, an impedance analyzer and a network analyzer can also be used as the measurement unit 5.

Note that the measurement unit 5 may conduct measurement only in a frequency or frequency band used by the extraction unit 2, the evaluation unit 3, and the classification unit 4, but may also measure the electrical characteristic in a wide band by changing frequencies so as to extract the frequency or frequency band used for evaluation from the obtained spectrum.

Data Processing Unit 6

The data processing unit 6 removes noise from chronological change data of the electrical characteristic of blood, which has been measured in the measurement unit 5. In the data processing unit 6, a method for removing noise is not particularly limited, and various methods for removing noise may be employed. For example, the reliability of a signal of the electrical characteristic measured by fitting or the like may be evaluated so as to select the method for removing noise in accordance with the result. In this event, processing is also possible by combining a plurality of noise removal methods.

Storage Unit

The storage unit stores chronological change data of electrical characteristic of blood, which has been measured by the measurement unit 5, data from which noise has been removed by the data processing unit 6, the result of evaluation in the evaluation unit 3, the result of classification in the classification unit 4, and the like. The storage unit is configured from a hard disk, for example.

Display Unit

The display unit displays chronological change data of the electrical characteristic of blood, which has been measured by the measurement unit 5, data from which noise has been removed by the data processing unit 6, the result of evaluation in the evaluation unit 3, the result of classification in the classification unit 4, and the like. The display unit may have any configuration by which these can be viewed.

Operation

Figure 7:
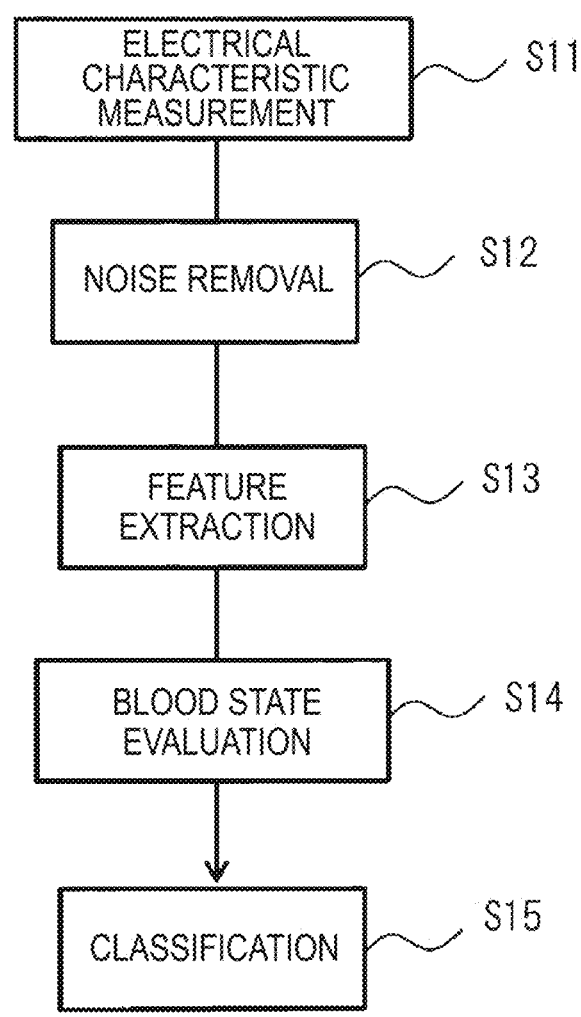
FIG. 7 is a flowchart illustrating a method for analyzing a state of blood by using a blood state analysis device 10 illustrated in FIG. 6, in the order of steps.

Next, the operation of the above-described blood state analysis device 10, that is, a method for evaluating and classifying the state of blood by using the blood state analysis device 10 will be described. FIG. 7 is a flowchart illustrating a method for analyzing the state of blood by using the blood state analysis device 10 illustrated in FIG. 6, in the order of steps.

Step S11: Electrical Characteristic Measurement Step

In the blood state analysis device 10 according to the modification example, first, in the measurement unit 5, the electrical characteristic of blood being an analysis target is measured chronologically in a particular frequency or frequency band. In this event, conditions for measuring the electrical characteristic are not limited to particular conditions, and can be set as appropriate depending on the kind of electrical characteristic as long as the blood being the analysis target is not altered.

The measurement may be conducted in a frequency or frequency band that is used in an extraction step, an evaluation step, and a classification step, or the electrical characteristic may be measured in a wide band including all the frequencies and frequency bands that are used. In this case, from the obtained spectrum, a frequency or frequency band used for evaluation is extracted in the extraction unit 2 and the evaluation unit 3.

Step S12: Noise Removal Step

Next, in the data processing unit 6, by various noise removal methods, noise is removed from the data signal measured by the measurement unit 5. In this event, for example, the reliability of a signal of the electrical characteristic measured by fitting or the like may be evaluated so as to select the method for removing noise in accordance with the result. In this event, processing is also possible by combining a plurality of noise removal methods.

Steps S13 to S15

A feature extraction step in step S13, a blood state evaluation step in step S14, and a classification step in step S15 are the same as the steps S1 to S3 in the above-described blood state analysis device according to the first embodiment.

As specifically described above, also in the blood state analysis device according to the modification example, blood is evaluated and classified by use of the feature extracted from chronological change data of the electrical characteristic. Therefore, the state of blood can be analyzed highly precisely by a simple method. In addition, in the blood state analysis device according to the modification example, data from which noise is removed in the data processing unit 6 is used, and thus, the evaluation and classification are performed more precisely.

3. Second Embodiment

Figure 8:
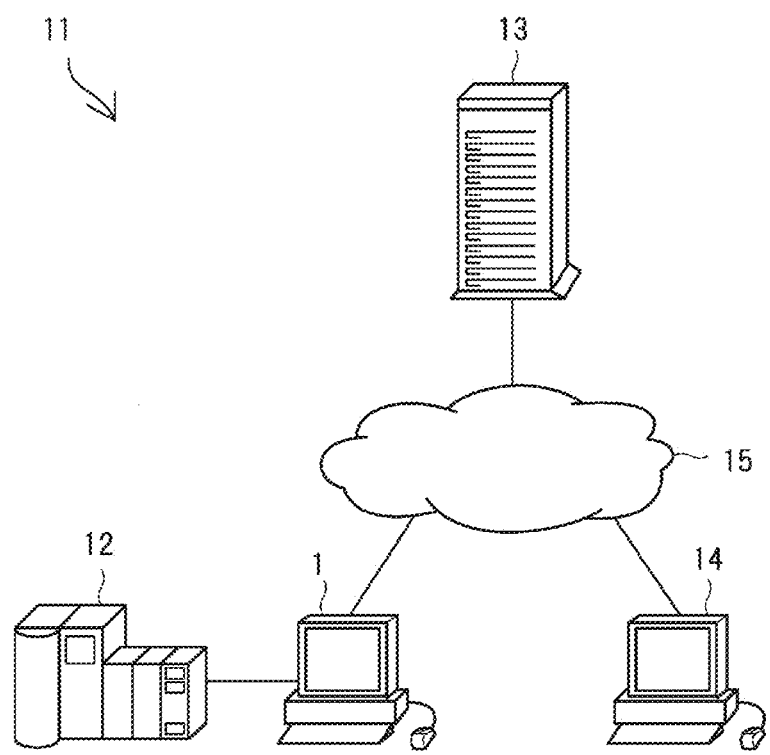
FIG. 8 is a diagram illustrating a schematic configuration of a blood state analysis system according to a second embodiment of the present disclosure.

Next, a blood state analysis system according to a second embodiment of the present disclosure will be described. FIG. 8 is a diagram illustrating a schematic configuration of the blood state analysis system according to the present embodiment. As illustrated in FIG. 8, a blood state analysis system 11 according to the present embodiment includes the above-described blood state analysis device 1 according to the first embodiment and an electrical characteristic measurement device 12. The blood state analysis system 10 according to the present embodiment may be connected to a server 13, a display device 14, and the like, as necessary.

Electrical Characteristic Measurement Device 12

The electrical characteristic measurement device 12 includes a measurement unit that is configured to apply a voltage between a pair of electrodes provided in a sample container to be filled with blood being the analysis target, and to chronologically measure an electrical characteristic of the blood in a particular frequency or frequency band. A configuration of the electrical characteristic measurement device 12 is not particularly limited, and may be appropriately determined in accordance with the electrical characteristic to be measured. For example, when an alternating voltage is applied between a pair of electrodes to measure the impedance and dielectric permittivity of blood, an impedance analyzer and a network analyzer can also be used.

Server 13

The server 13 is connected to the blood state analysis device 1 and the display device 14 through a network 15, and includes an information storage unit, for example. Further, the server 13 manages various kinds of data uploaded from the blood state analysis device 1, and outputs data to the display device 14 and the blood state analysis device 1 in response to a request.

Display Device 14

The display device 14 displays data of the electrical characteristic measured by the electrical characteristic measurement device 12, the result of evaluation and classification by the blood state analysis device 1, and the like. The display device 14 may be provided with an information input unit so that a user can select and input data to be displayed. In this case, information inputted by the user is transmitted to the server 13 and the blood state analysis device 1 through the network 15.

Also in the blood state analysis system 11 according to the present embodiment, since the blood is evaluated and classified by use of the feature extracted from chronological change data of the electrical characteristic, it is possible to analyze the state of blood highly precisely by a simple method.

Additionally, the present technology may also be configured as below.

(1)

A blood state analysis device including at least:

an extraction unit configured to extract at least one feature from chronological change data of an electrical characteristic of blood in two or more frequency bands;

an evaluation unit configured to evaluate a state of the blood on the basis of the at least one feature extracted by the extraction unit; and a classification unit configured to classify the blood on the basis of a result of evaluation conducted by the evaluation unit.

(2)

The blood state analysis device according to (1), wherein the evaluation unit digitalizes the at least one extracted feature for each frequency band.

(3)

The blood state analysis device according to (1) or (2), wherein the classification unit classifies the blood by use of a numerical value representing the at least one feature.

(4)

The blood state analysis device according to (3), wherein the classification unit classifies the blood by comparing the numerical value with a predetermined threshold.

(5)

The blood state analysis device according to (3) or (4), wherein the numerical value is a change amount $\delta A$ $(=A(f_x,t_y)/A(f_x,t_a))$ of an electrical characteristic value A in a given frequency $f_x$ from a reference time $t_a$ to a given time $t_y$.

(6)

The blood state analysis device according to any one of (1) to (5), wherein the at least one feature is a distinctive time associated with a change in a state of the blood.

(7)

The blood state analysis device according to any one of (1) to (6), wherein the classification unit classifies the blood by use of a number of change points in a frequency gradient and/or a direction in which the frequency gradient changes.

(8)

The blood state analysis device according to any one of (1) to (7), wherein the classification unit classifies the blood by comparing features of each frequency band graphically.

(9)

The blood state analysis device according to any one of (1) to (8), wherein the extraction unit extracts at least one feature in two or more frequency bands in a range of from 100 Hz to 100 MHz.

(10)

The blood state analysis device according to any one of (1) to (9), further including:

a measurement unit configured to chronologically measure the electrical characteristic of the blood, which is an analysis target, in a particular frequency or frequency band.

(11)

The blood state analysis device according to (10), including:

a data processing unit configured to remove noise from the chronological change data of the electrical characteristic of the blood, which has been measured by the measurement unit.

(12)

A blood state analysis system including:

an electrical characteristic measurement device including a measurement unit configured to chronologically measure an electrical characteristic of blood, which is an analysis target, in a particular frequency or frequency band; and a blood state analysis device including at least an extraction unit configured to extract a feature from chronological change data of the electrical characteristic of the blood, which has been measured by the electrical characteristic measurement device, in two or more frequency bands, an evaluation unit configured to evaluate the blood on the basis of the feature extracted by the extraction unit, and a classification unit configured to classify the blood on the basis of a result of evaluation conducted by the evaluation unit.

(13)

The blood state analysis system according to (12), further including:

a server including an information storage unit configured to store information of at least one of a result of measurement in the electrical characteristic measurement device, the feature extracted by the extraction unit of the blood state analysis device, the result of evaluation in the evaluation unit of the blood state analysis device, and a result of classification in the classification unit of the blood state analysis device, wherein the server is connected to the electrical characteristic measurement device and/or the blood state analysis device through a network.

(14)

A blood state analysis method including:

an extraction step of extracting a feature from chronological change data of an electrical characteristic of blood in two or more frequency bands;

an evaluation step of evaluating the blood on the basis of the feature extracted by the extraction unit; and a classification step of classifying the blood on the basis of a result of evaluation conducted by the evaluation unit.

(15)

A program for causing a computer to execute:

an extraction function of extracting a feature from chronological change data of an electrical characteristic of blood in two or more frequency bands;

an evaluation function of evaluating the blood on the basis of the extracted feature; and a classification function of classifying the blood on the basis of a result of evaluation.

Note that the effects described in the present specification are examples and not limiting, and other effects may be exhibited.

EXAMPLES

Hereinafter, effects of the present disclosure will be specifically described. In the present example, the thrombosis risk was evaluated using the above-described blood state analysis device according to the first embodiment by the following method, and blood was classified on the basis of the evaluation result. FIGS. 9, 10, 12, 14, and 17 are diagrams illustrating evaluation and classification methods according to Examples 1 to 6.

Example 1

Figure 9:
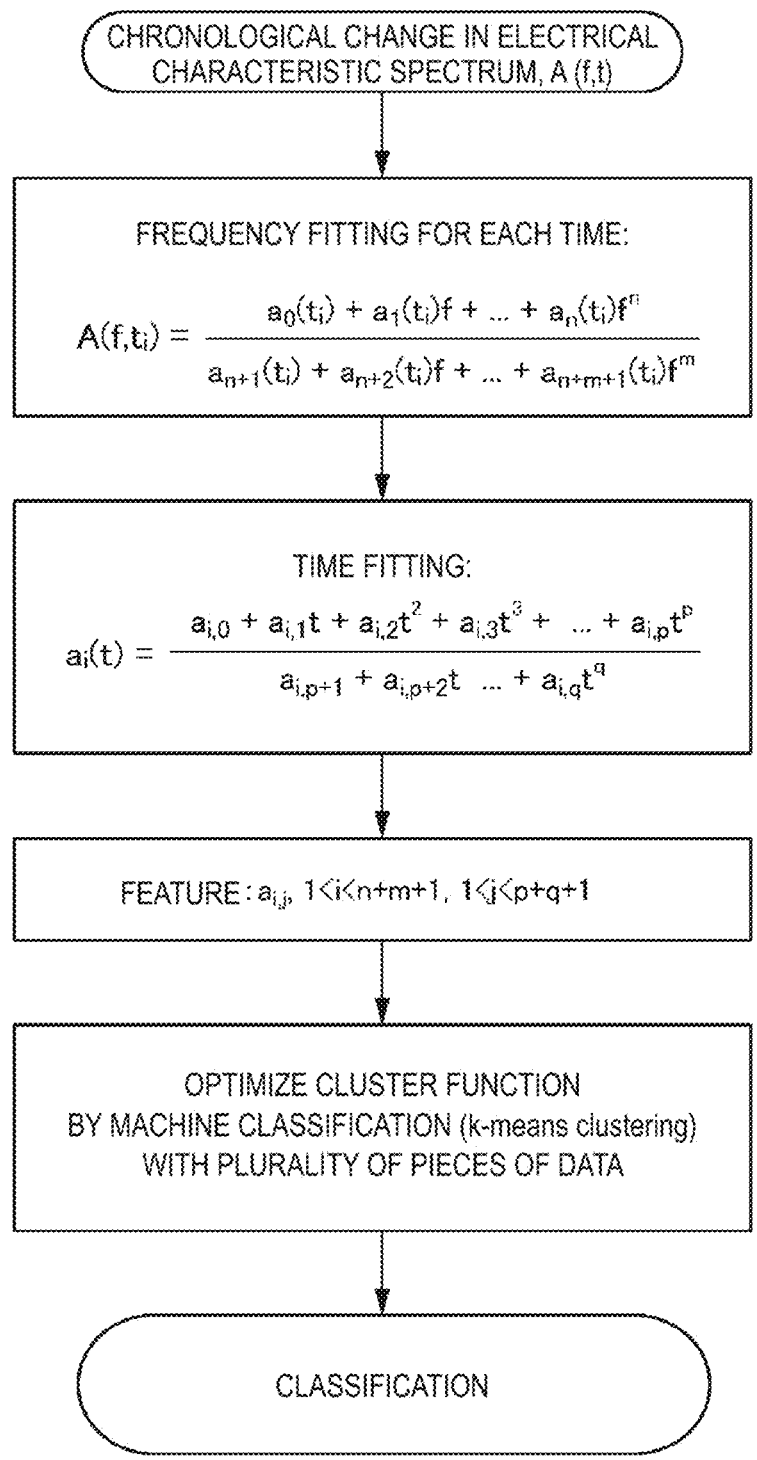
FIG. 9 is a diagram illustrating an evaluation and classification method according to Example 1.

The state of blood was evaluated and classified by fitting chronological change data of an electrical characteristic by time and frequency by the method illustrated in FIG. 9. The results are shown in Table 2 below.

TABLE 2

|  |  | True State | |
|---|---|---|---|
|  |  | Positive | Negative |
| Test Results | Positive | True Positive 5 | False Positive 1 |
|  | Negative | False Negative 1 | True Negative 4 |
|  |  | Sensitivity 83% | Specificity 80% |

As illustrated in Table 2, this method enables classification of blood of a patient with thrombosis at a satisfactory score of a sensitivity being 83% and a specificity being 80%.

Here, the "sensitivity" and the "specificity" are indexes used in laboratory tests. The "sensitivity" is a value defined as the "possibility at which an object that is supposed to be determined to be positive is correctly determined to be positive", and the "specificity" is the "possibility at which an object that is negative is correctly determined to be negative". In addition, it is preferable that each of these values is high, and a method by which high values are obtained for both the "sensitivity" and the "specificity" is an excellent testing method. However, when setting a threshold, a priority to the sensitivity results in a lower specificity, whereas a priority to the specificity results in a lower sensitivity. Accordingly, the threshold is typically set in a manner that both values can be within acceptable ranges.

Example 2

Figure 10:
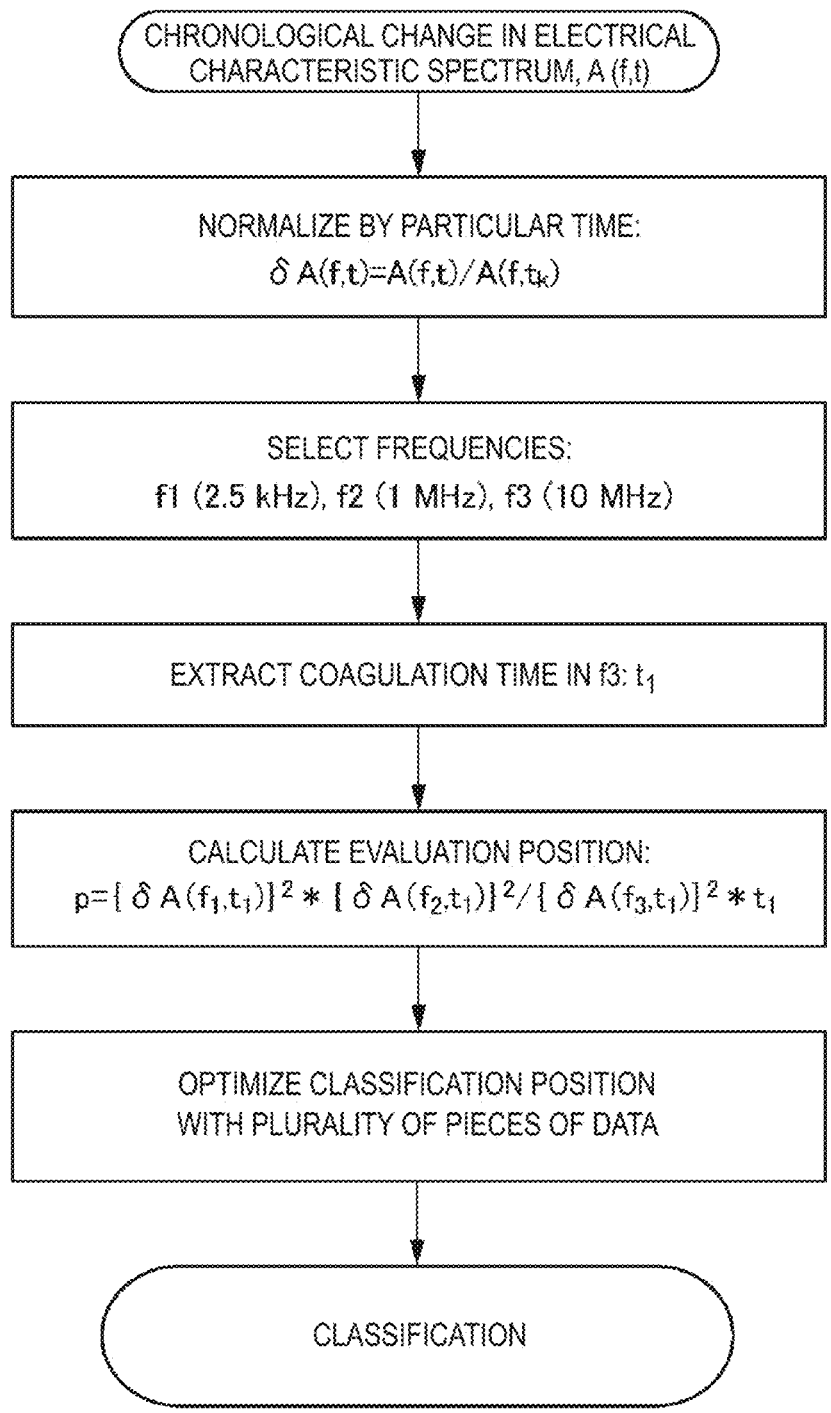
FIG. 10 is a diagram illustrating an evaluation and classification method according to Example 2.
Figure 11:
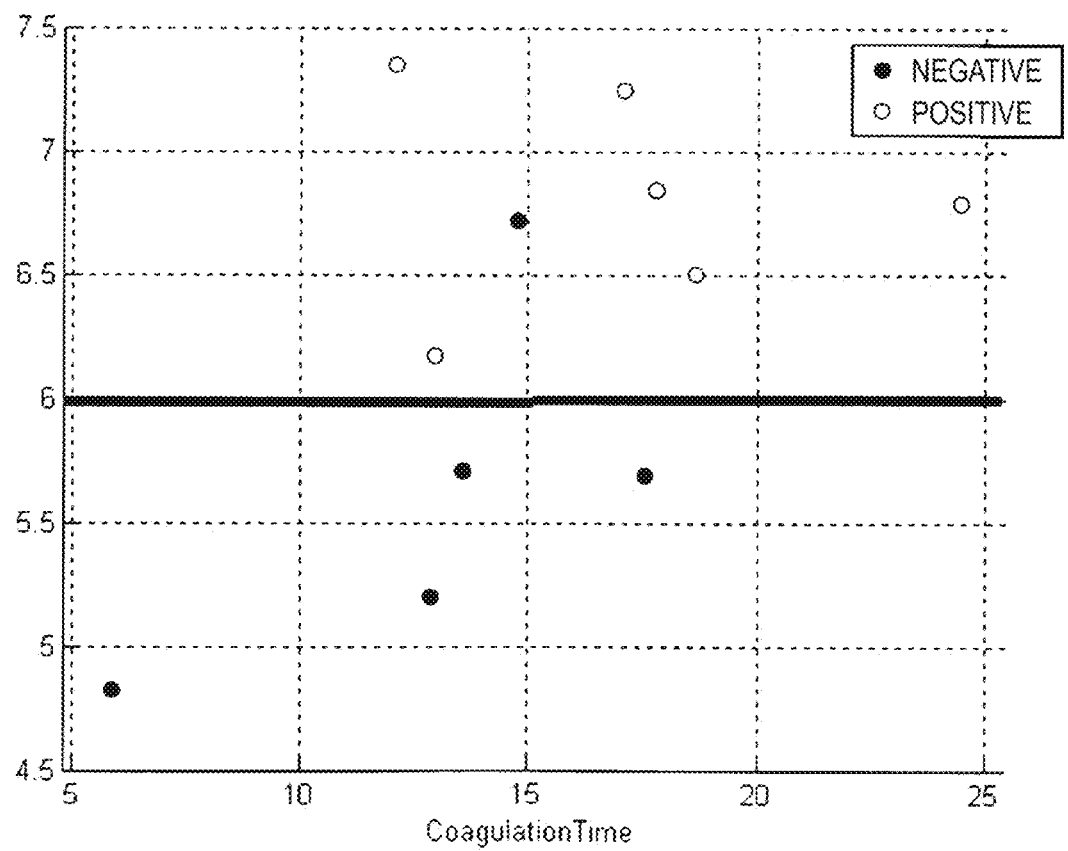
FIG. 11 is a diagram illustrating a classification result according to Example 2.

Next, the state of blood was evaluated and classified by a method in which chronological change data of a complex dielectric permittivity spectrum of blood illustrated in FIG. 10 was normalized by a particular time and then the determination value $p_1$ represented by the above-described formula 2 was used. In this event, $f_1$ was 2.5 kHz, $f_2$ was 1 MHz, $f_3$ was 10 MHz, and a coagulation time $t_1$ was obtained. The resulting determination value $p_1$ was classified by a predetermined threshold as illustrated in FIG. 11, and was evaluated. The results are shown in Table 3 below.

TABLE 3

|  |  | True State | |
|---|---|---|---|
|  |  | Positive | Negative |
| Test Results | Positive | True Positive 6 | False Positive 1 |
|  | Negative | False Negative 0 | True Negative 4 |
|  |  | Sensitivity 100% | Specificity 80% |

As illustrated in Table 3, this method enables classification of blood of a patient with thrombosis at a satisfactory score of a sensitivity being 100% and a specificity being 80%.

Example 3

Figure 12:
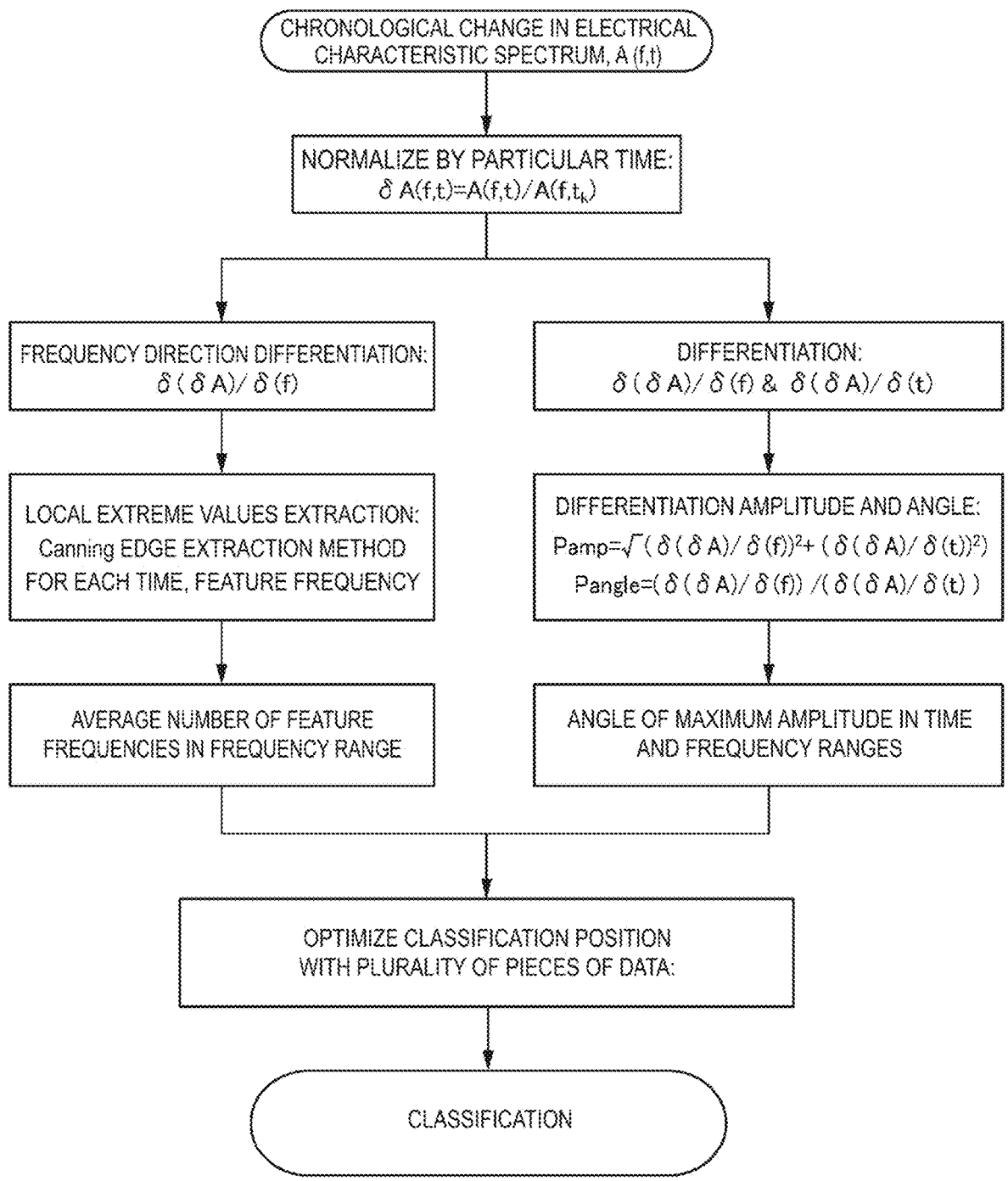
FIG. 12 is a diagram illustrating an evaluation and classification method according to Example 3.
Figure 13:
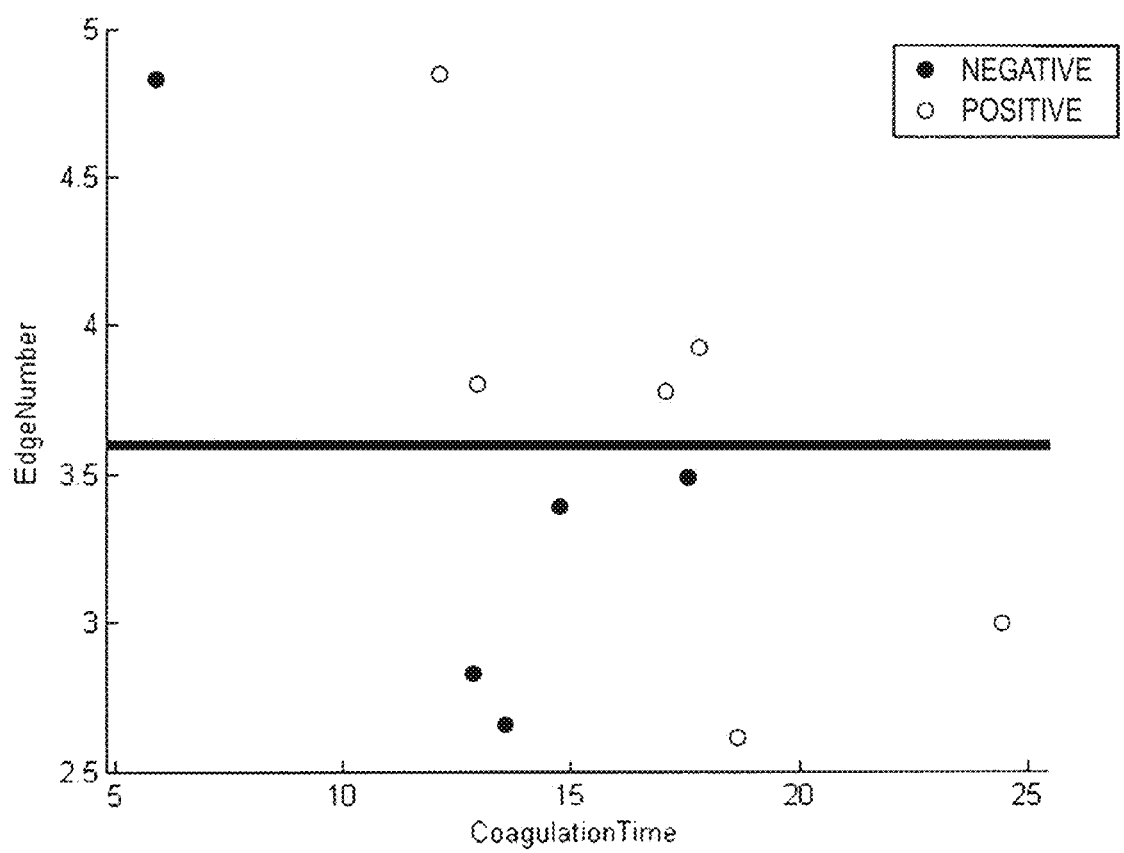
FIG. 13 is a diagram illustrating a classification result according to Example 3.

Next, evaluation and classification were conducted by a method illustrated in FIG. 12 using complex dielectric permittivity as an electrical characteristic. Specifically, chronological change data of a complex dielectric permittivity spectrum of blood was normalized by a particular time and then the number of change points in a frequency gradient was classified by a predetermined threshold as illustrated in FIG. 13, and was evaluated. The results are shown in Table 4 below.

TABLE 4

|  |  | True State | |
|---|---|---|---|
|  |  | Positive | Negative |
| Test Results | Positive | True Positive 4 | False Positive 1 |
|  | Negative | False Negative 2 | True Negative 4 |
|  |  | Sensitivity 67% | Specificity 80% |

As illustrated in Table 4, this method enables classification of blood of a patient with thrombosis at a satisfactory score of a sensitivity being 67% and a specificity being 80%.

Example 4

Figure 14:
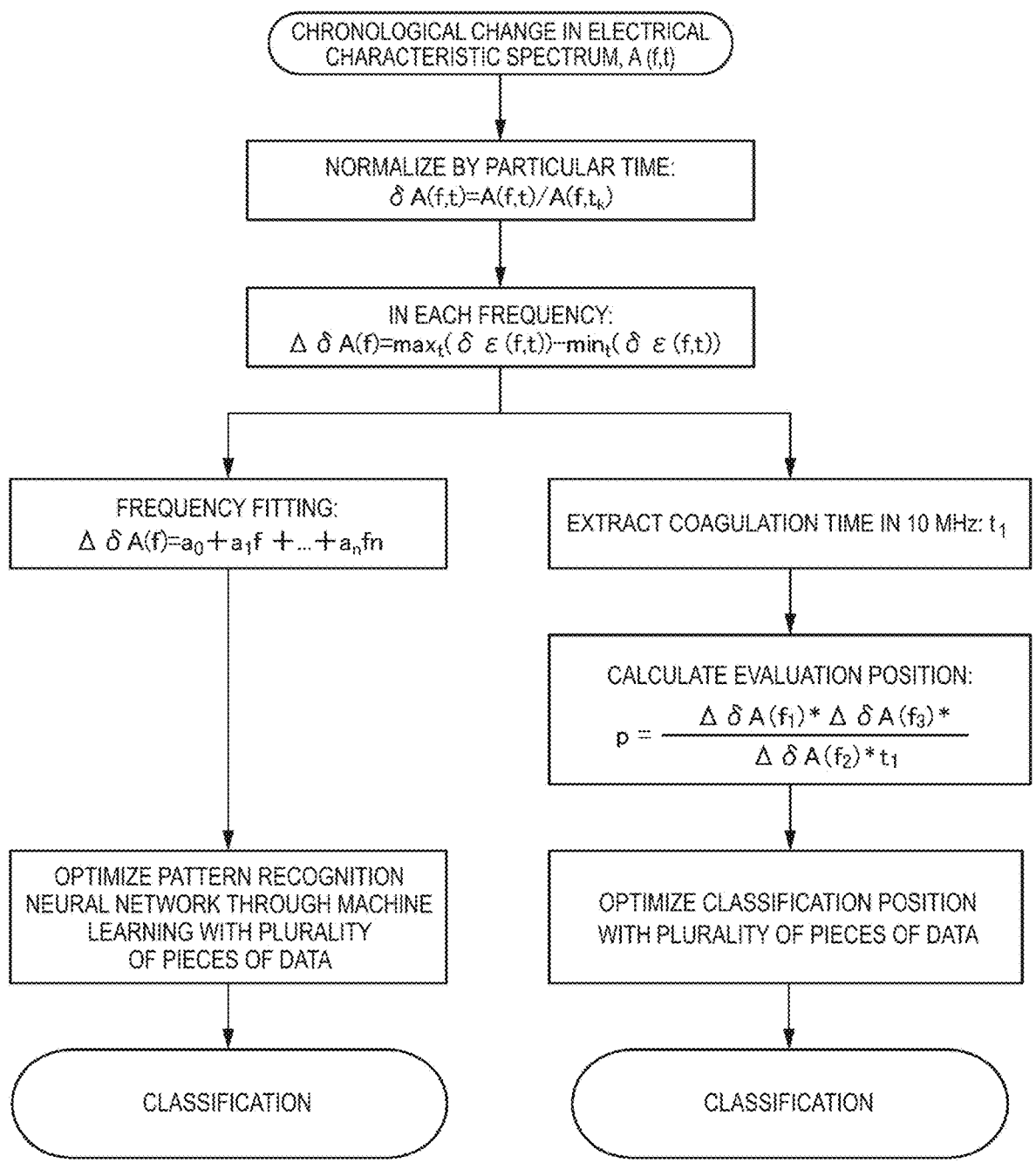
FIG. 14 is a diagram illustrating evaluation and classification methods according to Examples 4 and 5.
Figure 15:
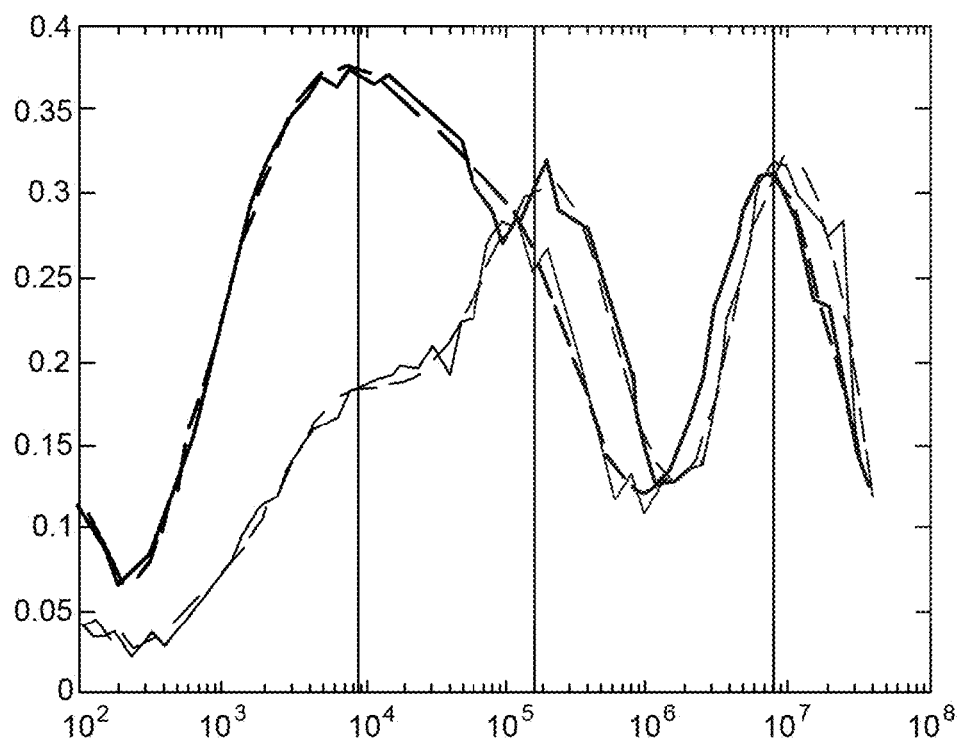
FIG. 15 is a diagram illustrating frequency fitting according to Example 4.

Evaluation and classification were conducted by a method using frequency fitting illustrated in FIG. 14 by using complex dielectric permittivity as an electrical characteristic. Specifically, chronological change data of a complex dielectric permittivity spectrum of blood was normalized by a particular time, and then a change amount Ac was calculated in each frequency. Evaluation was conducted by frequency fitting illustrated in FIG. 15, and classification was conducted. The results are shown in Table 5 below.

TABLE 5

|  |  | True State | |
| --- | --- | --- | --- |
|  |  | Positive | Negative |
| Test Results | Positive | True Positive 4 | False Positive 0 |
|  | Negative | False Negative 2 | True Negative 5 |
|  |  | Sensitivity 67% | Specificity 100% |

As illustrated in Table 5, this method enables classification of blood of a patient with thrombosis at a satisfactory score of a sensitivity being 67% and a specificity being 100%.

Example 5

Figure 16:
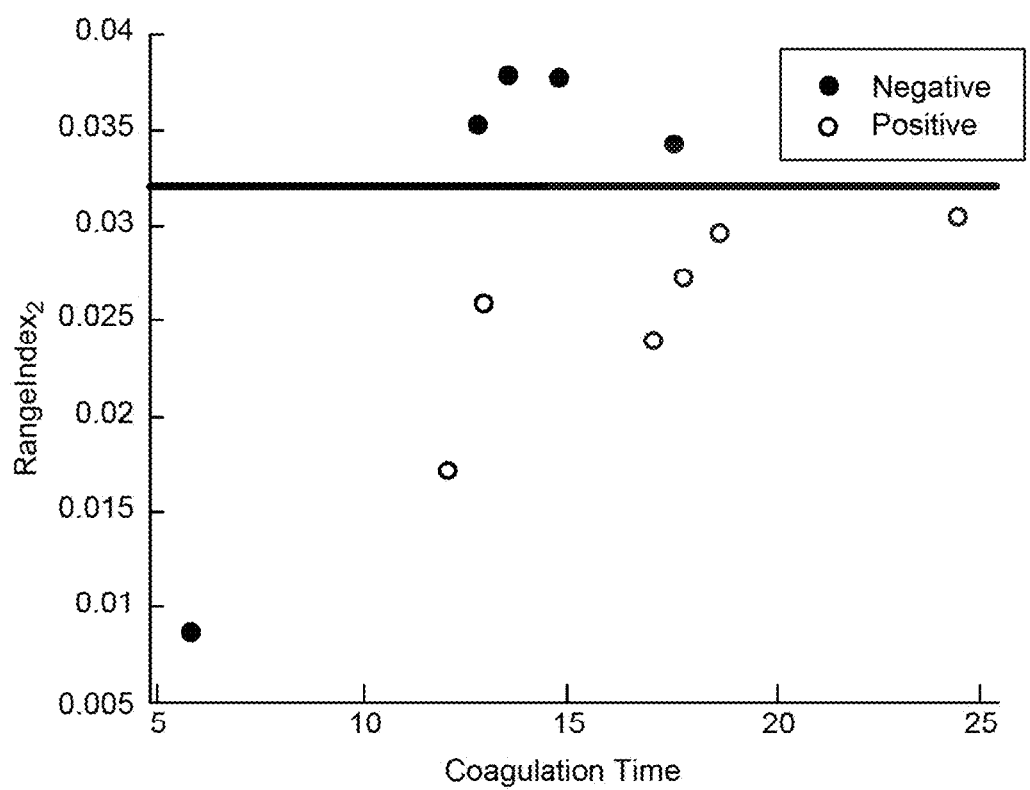
FIG. 16 is a diagram illustrating a classification result according to Example 5.

Evaluation and classification were conducted by a method using a coagulation time illustrated in FIG. 14 by using complex dielectric permittivity as an electrical characteristic. Specifically, instead of frequency fitting in the above-described Example 4, the coagulation time was extracted in 10 MHz, and on the basis of this value, classification was conducted by a predetermined threshold as illustrated in FIG. 16, and evaluation was conducted. The results are shown in Table 6 below.

TABLE 6

|  |  | True State | |
| --- | --- | --- | --- |
|  |  | Positive | Negative |
| Test Results | Positive | True Positive 6 | False Positive 1 |
|  | Negative | False Negative 0 | True Negative 4 |
|  |  | Sensitivity 100% | Specificity 80% |

As illustrated in Table 6, this method enables classification of blood of a patient with thrombosis at a satisfactory score of a sensitivity being 100% and a specificity being 80%.

Example 6

Figure 17:
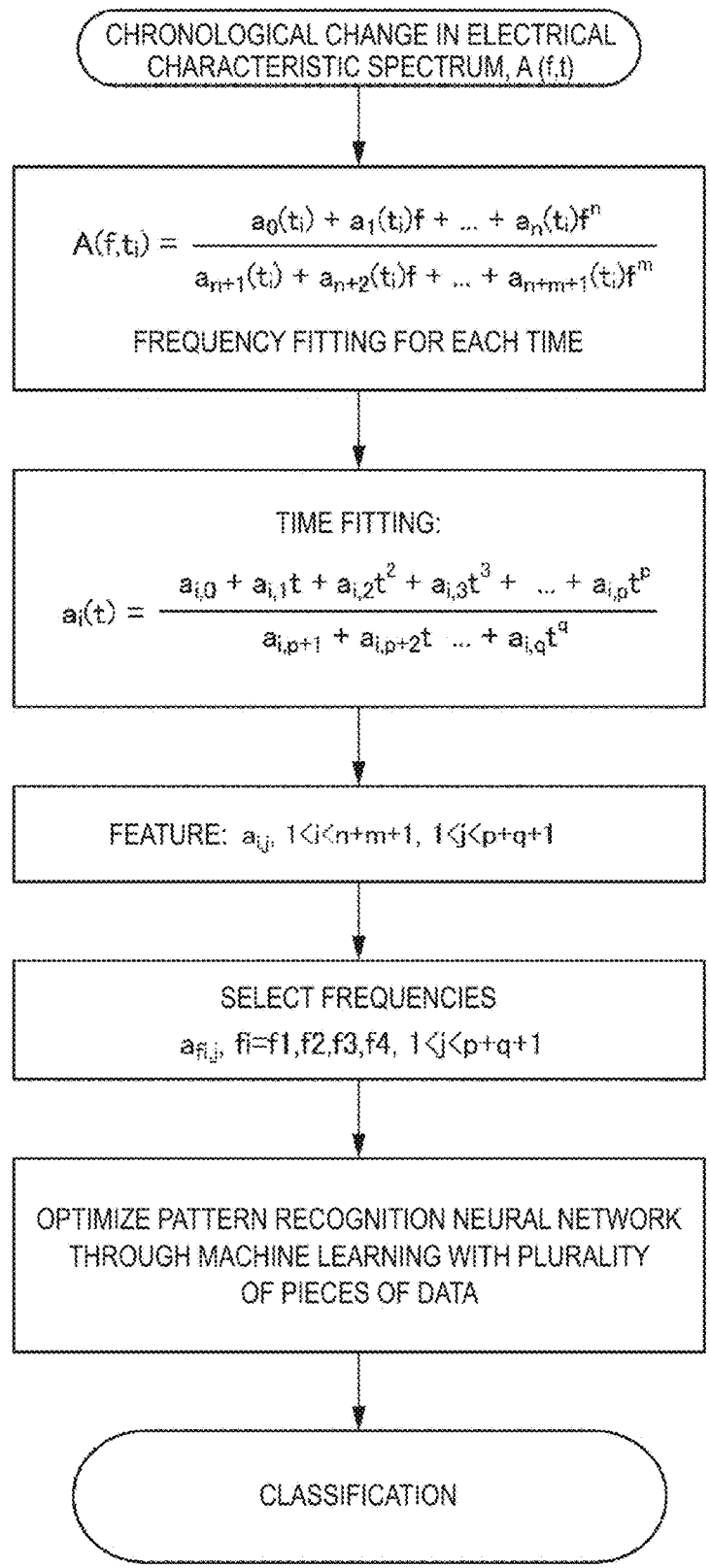
FIG. 17 is a diagram illustrating an evaluation and classification method according to Example 6.

Evaluation and classification were conducted by a method illustrated in FIG. 17 by using complex dielectric permittivity as an electrical characteristic. Specifically, chronological change data of a complex dielectric permittivity spectrum of blood was normalized by a particular time and then fitting was conducted by frequency and time. Then, from the obtained data, four frequencies were selected, and the state of blood was evaluated by a pattern recognition neural network through machine learning, and classification was conducted. The results are shown in Table 7 below.

TABLE 7

|  |  | True State | |
| --- | --- | --- | --- |
|  |  | Positive | Negative |
| Test Results | Positive | True Positive 5 | False Positive 3 |
|  | Negative | False Negative 1 | True Negative 2 |
|  |  | Sensitivity 83% | Specificity 67% |

As illustrated in Table 7, this method also enables classification of blood of a patient with thrombosis at a satisfactory score of a sensitivity being 83% and a specificity being 67%.

REFERENCE SIGNS LIST 1, 10 blood state analysis device
2 extraction unit
3 evaluation unit
4 classification unit
5 measurement unit
6 data processing unit
11 blood state analysis system
12 electrical characteristic measurement device
13 server
14 display device
15 network

The invention claimed is:
1. A blood state analysis device comprising:
a processing device and a memory device containing instructions that, when executed by the processing device, are configured to:
extract at least one feature from chronological change data of an electrical characteristic of blood of a patient in two or more frequency bands;
evaluate a state of the blood of the patient on the basis of the at least one extracted feature;
classify the blood of the patient according to thrombosis risk on the basis of a result of the evaluation, wherein the blood is classified by use of a numerical value representing the at least one extracted feature and wherein the numerical value is a change amount $\delta A$ (=A (fx,ty)/A (fx,ta)) of an electrical characteristic value A of the blood at a given frequency fx from a reference time ta to a given time ty; and
output an indication of thrombosis risk of the patient based on the classification of the blood of the patient and, upon indication of thrombosis risk, instruct administration of an anti-platelet aggregation agent or an anti-coagulant agent to the patient.
2. The blood state analysis device according to claim 1, wherein the at least one extracted feature for each frequency band is digitized.
3. The blood state analysis device according to claim 1, wherein the blood is classified by comparing the numerical value with a predetermined threshold.
4. The blood state analysis device according to claim 1, wherein the at least one feature is a distinctive time associated with a change in a state of the blood.
5. The blood state analysis device according to claim 1, wherein the blood is classified by use of a number of change points in a frequency gradient and/or a direction in which the frequency gradient changes.

6. The blood state analysis device according to claim 1, wherein the blood is classified by comparing features of each frequency band graphically.

7. The blood state analysis device according to claim 1, wherein the instructions are further configured to:
chronologically measure the electrical characteristic of the blood, which is an analysis target, in a particular frequency or frequency band.

8. The blood state analysis device according to claim 7, wherein the instructions are further configured to:
remove noise from the chronological change data of the measured electrical characteristic of the blood.

9. The blood state analysis device according to claim 1, wherein the frequency fx is in a range from 3 MHz to 15 MHz.

10. The blood state analysis device according to claim 1, wherein the anti-platelet aggregation agent consists of acetylsalicylic acid and the anti-coagulant agent is selected from a group consisting of warfarin, heparin, activated blood coagulation factor Xa inhibitors and direct thrombin inhibitors.

11. A blood state analysis system comprising:
an electrical characteristic measurement device including
an electrical characteristic measurement device that chronologically measures an electrical characteristic of blood of a patient, which is an analysis target, in a particular frequency or frequency band; and
a blood state analysis device including
a processing device and a memory device containing instructions that, when executed by the processing device, are configured to:
extract a feature from chronological change data of the measured electrical characteristic of the blood of the patient, in two or more frequency bands,
evaluate the blood of the patient on the basis of the extracted feature,
classify the blood of the patient according to thrombosis risk on the basis of a result of the evaluation, wherein the blood is classified by use of a numerical value representing the at least one extracted feature and wherein the numerical value is a change amount $\delta A$ (=A (fx,ty)/A (fx,ta)) of an electrical characteristic value A of the blood at a given frequency fx from a reference time to to a given time ty, and
output an indication of thrombosis risk of the patient based on the classification of the blood of the patient and, upon indication of thrombosis risk, instruct administration of an anti-platelet aggregation agent or an anti-coagulant agent to the patient.

12. The blood state analysis system according to claim 11, further comprising:
a server including
a data storage device that stores information of at least one of a result of measurement in the electrical characteristic measurement device, the extracted feature, a result of the evaluation, and a result of the classification,
wherein the server is connected to the electrical characteristic measurement device and/or the blood state analysis device through a network.

13. A blood state analysis method comprising:
extracting a feature from chronological change data of an electrical characteristic of blood of a patient in two or more frequency bands;
evaluating the blood of a patient on the basis of the extracted feature;
classifying the blood of the patient according to thrombosis risk on the basis of a result of the evaluation, wherein the blood is classified by use of a numerical value representing the extracted feature and wherein the numerical value is a change amount $\delta A$ (=A (fx,ty)/A (fx,ta)) of an electrical characteristic value A of the blood at a given frequency fx from a reference time ta to a given time ty; and
outputting an indication of thrombosis risk of the patient based on the classification of the blood of the patient and, upon indication of thrombosis risk, instructing administration of an anti-platelet aggregation agent or an anti-coagulant agent to the patient.

14. A non-transitory computer-readable medium containing instructions that, when executed by a processing device, cause the processing device to execute a blood state analysis method comprising:
extracting a feature from chronological change data of an electrical characteristic of blood of a patient in two or more frequency bands;
evaluating the blood of the patient on the basis of the extracted feature;
classifying the blood of the patient according to thrombosis risk on the basis of a result of the evaluation, wherein the blood is classified by use of a numerical value representing the extracted feature and wherein the numerical value is a change amount $\delta A$ (=A (fx,ty)/A (fx,ta)) of an electrical characteristic value A of the blood at a given frequency fx from a reference time ta to a given time ty; and
outputting an indication of thrombosis risk of the patient based on the classification of the blood of the patient and, upon indication of thrombosis risk, instructing administration of an anti-platelet aggregation agent or an anti-coagulant agent to the patient.

* * * * *